(12) United States Patent
Johnson

(10) Patent No.: US 6,428,559 B1
(45) Date of Patent: Aug. 6, 2002

(54) REMOVABLE, VARIABLE-DIAMETER VASCULAR FILTER SYSTEM

(75) Inventor: Kirk Johnson, Weston, FL (US)

(73) Assignee: Cordis Corporation, Miami Lakes, FL (US)

(*) Notice: Subject to any disclaimer, the term of this patent is extended or adjusted under 35 U.S.C. 154(b) by 0 days.

(21) Appl. No.: 09/824,975

(22) Filed: Apr. 3, 2001

(51) Int. Cl.$^7$ .............................................. A61M 29/00
(52) U.S. Cl. ..................... 606/200; 606/139; 604/103.3
(58) Field of Search ................................ 606/200, 159, 606/191, 195, 127, 128, 180, 194, 198, 139; 604/22, 104, 96, 101

(56) References Cited

U.S. PATENT DOCUMENTS

| | | | |
|---|---|---|---|
| 3,620,212 A | * | 11/1971 | Fannon, Jr. et al. ........ 128/839 |
| 3,834,394 A | * | 9/1974 | Hunter et al. ................ 604/907 |
| 3,952,747 A | | 4/1976 | Kimmell, Jr. |
| 4,545,390 A | | 10/1985 | Leary |
| 4,619,274 A | | 10/1986 | Morrison |
| 4,665,906 A | | 5/1987 | Jervis |
| 4,688,553 A | | 8/1987 | Metals |
| 4,727,873 A | | 3/1988 | Mobin-Uddin |
| 4,925,445 A | | 5/1990 | Sakamoto et al. |
| 4,969,890 A | | 11/1990 | Sugita et al. |
| 4,984,581 A | | 1/1991 | Stice |
| 4,991,602 A | | 2/1991 | Amplatz et al. |
| 5,069,226 A | | 12/1991 | Yamauchi et al. |
| 5,095,915 A | | 3/1992 | Engelson |
| 5,171,383 A | | 12/1992 | Sagaye et al. |
| 5,597,378 A | | 1/1997 | Jervis |
| 5,695,519 A | | 12/1997 | Summers et al. |
| 5,769,816 A | | 6/1998 | Barbut et al. |
| 5,814,064 A | | 9/1998 | Daniel et al. |
| 5,827,324 A | | 10/1998 | Cassell et al. |
| 5,876,367 A | | 3/1999 | Kaganov et al. |
| 5,895,399 A | | 4/1999 | Barabut et al. |
| 5,910,154 A | | 6/1999 | Tsugita et al. |
| 5,911,734 A | | 6/1999 | Tsugita et al. |
| 6,001,118 A | | 12/1999 | Daniel et al. |
| 6,053,932 A | | 4/2000 | Daniel et al. |
| 6,066,149 A | * | 5/2000 | Samson et al. ............. 606/127 |
| 6,068,623 A | | 5/2000 | Zadno-Azizi et al. |
| 6,069,814 A | | 5/2000 | Liou et al. |
| 6,074,357 A | | 6/2000 | Kaganov et al. |
| 6,096,053 A | * | 8/2000 | Bates ......................... 606/159 |
| 6,152,946 A | | 11/2000 | Broome et al. |
| 6,171,328 B1 | | 1/2001 | Addis |
| 6,312,407 B1 | * | 11/2001 | Zadno-Azizi et al. ... 604/103.03 |

* cited by examiner

Primary Examiner—A. Vanatta
Assistant Examiner—Robert H. Muromoto, Jr.
(74) Attorney, Agent, or Firm—Paul A. Coletti

(57) ABSTRACT

A removable, variable-diameter vascular filter system comprising a guidewire and a filter which can be used to capture embolic particulates during medical procedures, while allowing for continuous perfusion of blood. The removable, variable-diameter vascular filter system allows the operator to vary the diameter of the filter, so that a single device can be used to capture embolic particulates in vessels with different lumenal diameters.

22 Claims, 2 Drawing Sheets

REMOVABLE, VARIABLE-DIAMETER VASCULAR FILTER SYSTEM

BACKGROUND

1. Field of the Invention

The present invention relates to the treatment of vascular disease, and more particularly to a removable, variable-diameter vascular filter system for use during medical procedures.

2. Discussion of Related Art

Percutaneous transluminal coronary angioplasty (PTCA), stenting and atherectomy are therapeutic medical procedures used to increase blood flow through the coronary arteries. These procedures can often be performed as alternatives to coronary bypass surgery. PTA (percutaneous transluminal angioplasty) and stenting can often be performed as alternatives to carotid endarterectomy, and femoral-popliteal bypass procedures. In PTA or PTCA procedures, the angioplasty balloon is inflated within the stenosed vessel, at the location of an occlusion, in order to shear and disrupt the wall components of the vessel to obtain an enlarged lumen. In stenting, an endoluminal prosthesis is implanted in the vessel to maintain patency following the procedure. In atherectomy, a rotating blade is used to shear plaque from the arterial wall.

One concern commonly encountered in all these techniques is the accidental release of portions of the plaque, thrombus or other embolic particulates, resulting in emboli which can lodge elsewhere in the vascular system. Such emboli may be extremely dangerous to the patient, and may result in myocardial infarction, stroke or limb ischemia.

In order to initiate these procedures, one must first introduce a guidewire into the lumen of the vessel to serve as a conduit for other interventional devices, such as angioplasty balloons and stent delivery systems. This guidewire must be advanced into a position past the location of the occlusion. Guidewires must be capable of traversing tortuous pathways within the body, consisting of bends, loops and branches. For this reason, guidewires need to be flexible, but they should also be sufficiently stiff to serve as a conduit for other devices. In addition, they must be "torqueable" to facilitate directional changes as they are guided into position. Guidewires are well known in the art, and are typically made of stainless steel, tantalum or other suitable materials, in a variety of different designs. For example, U.S. Pat. Nos. 4,545,390 and 4,619,274 disclose guidewires in which the distal segment is tapered for greater flexibility. The tapered section may be enclosed in a wire coil, typically a platinum coil, which provides increased column strength and torqueability. Another design is identified in U.S. Pat. No. 5,095,915, where the distal segment is encased in a polymer sleeve with axially spaced grooves to provide bending flexibility.

Vascular filters are also well known in the art, especially vena cava filters, as illustrated in U.S. Pat. Nos. 4,727,873 and 4,688,553. There is also a substantial amount of medical literature describing various designs of vascular filters and reporting the results of clinical and experimental use thereof. See, for example, the article by Eichelter and Schenk, entitled "Prophylaxis of Pulmonary Embolism," Archives of Surgery, Vol. 97 (August, 1968). See, also, the article by Greenfield, et al, entitled "A New Intracaval Filter Permitting Continued Flow and Resolution of Emboli'", Surgery, Vol. 73, No. 4 (1973).

Vascular filters are often used during a postoperative period, when there is a perceived risk of a patient encountering pulmonary embolism resulting from clots generated peri-operatively. Pulmonary embolism is a serious and potentially fatal condition that occurs when these clots travel to the lungs. The filter is therefore typically placed in the vena cava to catch and trap clots before they can reach the lungs.

Many of the vascular filters in the prior art are intended to be permanently placed in the venous system of the patient, so that even after the need for the filter has passed, the filter remains in place for the life of the patient. U.S. Pat. No. 3,952,747 describes a stainless steel filtering device that is permanently implanted transvenously within the inferior vena cava. This device is intended to treat recurrent pulmonary embolism. Permanent implantation is often deemed medically undesirable, but it is done because filters are implanted in patients in response to potentially life-threatening situations.

To avoid permanent implantation, it is highly desirable to provide an apparatus and method for preventing embolization associated with angioplasty, stenting or other procedures. In particular, it is desirable to provide a device which can be temporarily placed within the vascular system to collect and retrieve plaque, thrombus and other embolic particulates which have been dislodged during angioplasty, stenting or other procedures. Such a device is removed at the end of the procedure. U.S. Pat. Nos. 5,814,064 and 5,827,324 describe such a device, wherein the filter is expanded to a predetermined diameter through the introduction of a fluid or a gas. U.S. Pat. No. 5,910,154 describes a filter, which expands to a predetermined diameter through the use of a spring-based actuator. U.S. Pat. No. 6,053,932 describes a filter, which expands to a predetermined diameter through the use of a cinch assembly.

One concern commonly encountered with all these devices is that the filter opens to a single, predetermined diameter, thereby requiring an inventory of filters of different diameters, so as to insure that the proper size is available for the patient.

The prior art makes reference to the use of alloys such as Nitinol (Ni—Ti alloy), which have shape memory and/or superelastic characteristics, in medical devices that are designed to be inserted into a patient's body. The shape memory characteristics allow the devices to be deformed to facilitate their insertion into a body lumen or cavity, and then, when heated within the body, to return to their original shape. Superelastic characteristics, on the other hand, generally allow the metal to be deformed and restrained in the deformed condition to facilitate the insertion of the medical device containing the metal into a patient's body, with such deformation causing the phase transformation. Once within the body lumen, the restraint on the superelastic member can be removed, thereby reducing the stress therein so that the superelastic member can return to its original un-deformed shape by the transformation back to the original phase.

The prior art makes reference to the use of metal alloys having superelastic characteristics in medical devices which are intended to be inserted or otherwise used within a patient's body. See for example, U.S. Pat. No. 4,665,905 (Jervis).

Some guidewire designs have recommended the use of superelastic alloys. For example, U.S. Pat. No. 4,925,445 discloses a guidewire where the distal segment, and at least one portion of the proximal segment, is made from a superelastic alloy like Nitinol, where the transformation temperature from austenite to martensite occurs at 10° C. or below. Also, U.S. Pat. No. 4,984,581 discloses a guidewire having a core of shape memory alloy, where the shape memory properties of the alloy provide both tip-deflection and rotational movement in response to a controlled thermal stimulus.

However, the prior art has yet to disclose any guidewires, made from Nitinol or other suitable materials, incorporating removable, variable-diameter vascular filters, which can be used to address the clinical problem of collecting and retrieving portions of plaque, thrombus or other embolic particulates which have been dislodged during angioplasty, stenting or other procedures.

SUMMARY OF THE INVENTION

The present invention provides for a removable, variable-diameter vascular filter system which can be used to capture portions of plaque, thrombus or other embolic particulates dislodged during angioplasty, stenting or other procedures, and which overcomes many of the deficiencies associated with the prior art devices, as briefly described above.

In accordance with one aspect, the present invention is directed to a removable, variable-diameter vascular filter system comprising a guidewire having an outer diameter and an inner diameter, a proximal end and a distal end; a generally solid core wire having an outer diameter, a proximal end and a distal end, with the distal end slidably inserted into the proximal end of the guidewire, and advanced through the guidewire until the distal end of the core wire extends beyond the distal end of the guidewire; an end cap attached to the proximal end of the core wire; a spacer having a proximal end and a distal end, with the spacer removably mounted onto the core wire in a longitudinal direction such that the proximal end of the spacer is substantially in contact with the end cap; and a filter, comprising a proximal end and a distal end, a plurality of struts extending therebetween, and a porous covering permanently attached to the struts, with the proximal end of the filter attached to the distal end of the guidewire, and the distal end of the filter attached near the distal end of the core wire; the filter having a smaller first diameter for insertion into a vessel, and a larger second diameter for expanding to substantially equal the diameter of the lumen of the vessel and to be placed in a generally sealing relationship with the lumen of the vessel. The filter is placed distal to the occlusion to collect embolic particulates released during the medical procedure.

The advantage of the present invention is that the spacer can be used to vary the diameter of the filter, so that a single device can be used to capture embolic particulates in vessels of different lumenal diameters. In addition, the present invention eliminates the need for delivery sheaths, capture sheaths, and an inventory of systems with different diameter filters.

BRIEF DESCRIPTION OF DRAWINGS

The foregoing and other aspects of the present invention will best be appreciated with reference to the detailed description of the invention in conjunction with the accompanying drawings, wherein.

DETAILED DESCRIPTION OF THE PREFERRED EMBODIMENTS

The removable, variable-diameter vascular filter system of the present invention is designed to address the clinical problem of collecting and retrieving portions of plaque, thrombus or other embolic particulates which have been dislodged during angioplasty, stenting or other procedures, in vessels of various diameters, while allowing for continuous perfusion of blood. The device comprises a guidewire; a core wire inserted through the guidewire which is used to control the diameter of the filter; a filter comprising a proximal end and a distal end, a plurality of struts extending therebetween, and a porous covering permanently attached to the struts, with the proximal end of the filter attached to the distal end of the guidewire, and the distal end of the filter attached near the distal end of the core wire; a spacer removably mounted onto the proximal end of the guidewire in a longitudinal direction, which is in operational correspondence with the diameter of the filter; and an end cap attached to the proximal end of the core wire. The filter may be placed distal to the occlusion to collect embolic particulates released during the procedure.

Figure 1:
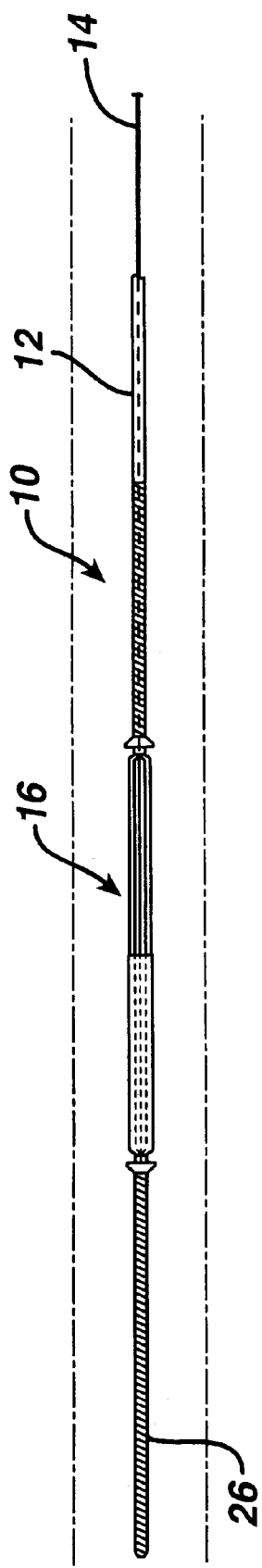
FIG. 1 is a simplified, cross-sectional view of an exemplary embodiment of the removable, variable-diameter vascular filter system with the filter in the closed position, in accordance with the present invention.
Figure 2:
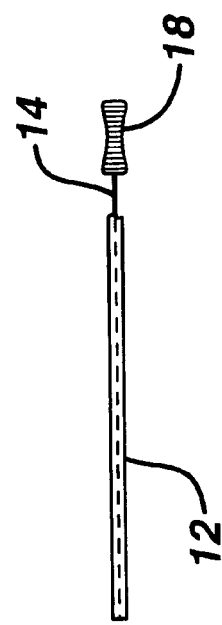
FIG. 2 is an enlarged, partial cross-sectional view of the proximal end of an exemplary embodiment of the removable, variable-diameter filter system when the filter is in the closed position, in accordance with the present invention.

While the present invention may be realized in a number of exemplary embodiments, for ease of explanation, one exemplary embodiment will be described in detail. Referring to the figures wherein like numerals indicate the same element throughout the views, there is shown in FIG. 1, a removable, variable-diameter vascular filter system 10 made in accordance with the present invention. The removable, variable-diameter vascular filter system comprises a guidewire 12, a core wire 14, and a filter 16 having a proximal end and a distal end, with the proximal end of the filter 16 attached to the distal end of the guidewire 12 and the distal end of the filter 16 attached near the distal end of the core wire 14. As illustrated in FIG. 1, the core wire 14 has been inserted into the guidewire 12 and is coaxially disposed within the guidewire 12 and the filter 16, and extends beyond the distal end of the filter to form the distal guidewire tip 26. Therefore, as illustrated in FIG. 1, the filter 16 has achieved its longest length and its smallest diameter and is in the closed position. FIG. 2 shows the proximal end of the guidewire 12, with the core wire 14 slidably inserted into the guidewire 12, and an end cap 18 attached to the proximal end of the core wire 14. As illustrated in FIG. 2, the core wire 14 can continue to be slidably advanced through the guidewire 12 until the end cap 18 is adjacent to but not in contact with the proximal end of the guidewire 12.

As illustrated in FIGS. 1 and 2, when the end cap 18 is adjacent to but not in contact with the guidewire 12, the distal end of said core wire 14 is positioned at its maximum distance from the distal end of said guidewire, and the filter 16 is in the closed position.

Figure 3:
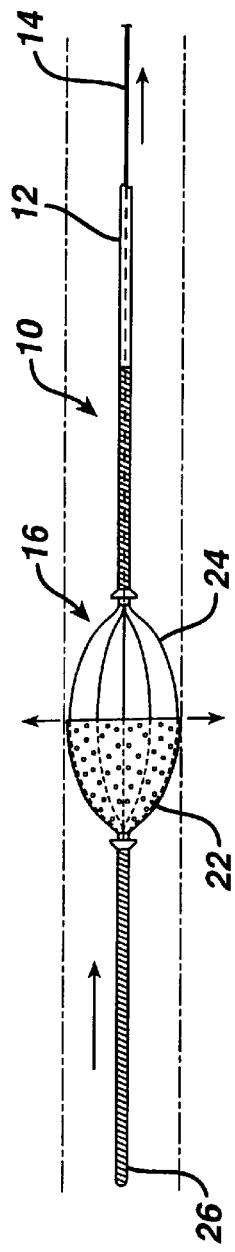
FIG. 3 is a view similar to FIG. 1, with the filter in the open position, in accordance with the present invention.
Figure 4:
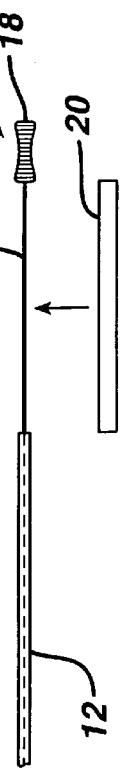
FIG. 4 is a view similar to FIG. 2, when the filter is in the open position, in accordance with the present invention.
Figure 5:
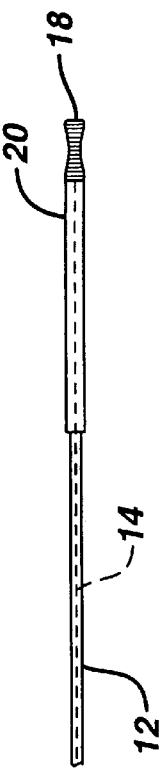
FIG. 5 is a view similar to FIG. 4, when the filter is in the open position and the spacer has been mounted on the guidewire, in accordance with the present invention.

FIG. 3 shows a removable, variable-diameter vascular filter system made in accordance with the present invention. The removable, variable-diameter vascular filter system comprises a guidewire 12, a core wire 14 slidably inserted into the guidewire 12, a filter 16, comprising a proximal end and a distal end and a plurality of struts 24 extending therebetween, with the proximal end of the filter 16 attached to the distal end of the guidewire 12, and the distal end of the filter 16 attached near the distal end of the core wire 14. As illustrated in FIG. 3, the core wire 14 has been slidably retracted through the guidewire 12, and the filter 16 is in the open position. FIGS. 4 and 5 show the proximal end of the guidewire 12, with the core wire 14 slidably inserted into the guidewire 12, an end cap 18 attached to the proximal end of the core wire 14, and a spacer 20 removably mounted on the proximal end of the core wire 14 and substantially in contact with the end cap 18 proximally and the guidewire 12 distally. As illustrated in FIGS. 3, 4 and 5, when the core wire 16 has been slidably retracted to allow the spacer to be mounted on the proximal end of the core wire 14, and when the proximal end of the guidewire 12 is substantially in contact with the distal end of the spacer 20, then the filter 16 is held in the open position, and the diameter of the filter 20 is in operational correspondence with the length of the spacer 20. The spacer 20 may be held in place by any number of suitable methods, and is preferably held in place by a snap or friction fit to the core wire 14. The variable-diameter vascular filter system may comprise a plurality of spacers to provide operational correspondence with a variety of filter diameters.

The removable, variable-diameter vascular filter system 10 may be made from any number of suitable materials, and is preferably made from a superelastic alloy such as Nitinol. The core wire 14 and the guidewire 12 may be coated with any number of lubricious, biocompatible coatings. The filter 16 may be made from any number of suitable materials, and is preferably made from a superelastic alloy such as Nitinol. The struts 24 may be made in any number of suitable configurations, and are preferably longitudinal struts, circumferential struts, or hingedly connected struts. The end cap 18 may be made from any number of suitable materials, and is preferably made from a metallic material. The end cap 18 may be attached to the core wire by any number of suitable methods, and is preferably welded onto the core wire 14. The spacer 20 may be made from any number of suitable materials, and is preferably made from polymeric material. The porous covering 22 on the filter 16 may be made from any number of suitable materials, and is preferably made from a flexible polymeric material with elastomeric properties chosen from a group consisting of polyurethane, polyethylene or a co-polymer thereof. The porous covering 22 on the filter 16 may comprise any number and configuration of pores and preferably comprises regularly-spacer laser-formed holes wherein the pore size is from about 20 to about 300 microns.

The exemplary embodiment of the removable, variable-diameter vascular filter system, as illustrated in FIGS. 1, 2, 3, 4 and 5, is used to collect and retrieve portions of plaque or thrombus which have been dislodged during angioplasty, stenting or other procedures by inserting it into the lumen of an occluded vessel, and then advancing it through the lumen until the distal end of the device is distal to the occlusion. At this point, the distal end of the core wire 14 has been slidably inserted into the proximal end of the guidewire 12, such that the core wire 14 is coaxially disposed within the guidewire 12 and the distal end of the core wire 14 extends beyond the distal end of the filter 14 to form the distal guidewire tip 26. The distal end of the core wire 14 is now at its maximum distance from the distal end of the guidewire 12, and the filter 16 is in the closed position, while at the proximal end of the core wire 14, the end cap 18 is adjacent to but not in contact with the guidewire 12. Before an angioplasty, stenting or other procedure is performed, the core wire 14 is retracted through the guidewire 12. The spacer 20 is mounted onto the proximal end of the core wire, with the proximal end of the spacer 20 substantially in contact with the distal end of the end cap 18.

When the proximal end of the guidewire 12 is substantially in contact with the distal end of the spacer 20, the filter will have achieved a desired diameter, in operational correspondence with the length of the spacer 20. Then, angioplasty, stenting or other procedures can be performed, with the filter capturing plaque, thrombus or other embolic particulates while allowing continuous perfusion of blood. After the procedure is complete, the spacer 20 is removed from the core wire 14. The core wire 14 is then advanced through the guidewire 12 until the distal end of the core wire 14 is at its maximum distance from the distal end of the guidewire 12, the distal end of the end cap 18 is adjacent to but not in contact with the proximal end of the guidewire 12, and the filter is in the closed position. The removable, variable-diameter filter system may then be removed from the lumen of the vessel.

Although shown and described are what are believed to be the preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

That which is claimed is:

1. A removable vascular filter system for insertion into a lumen of a vessel, said vascular filter system comprising:
   a) a guidewire having an outer diameter, an inner diameter, a proximal end and a distal end;
   b) a generally solid core wire having an outer diameter, a proximal end and a distal end, with said distal end slidably insertable into said proximal end of said guidewire and advanced through said guidewire until said distal end of said core wire extends beyond said distal end of said guidewire;
   c) an end cap having a proximal end and a distal end, with said distal end of said end cap attached to said proximal end of said core wire;
   d) a spacer having a proximal end and a distal end, said spacer removably mounted onto said core wire in a longitudinal direction such that said proximal end of said spacer is substantially in contact with said distal end of said end cap;
   e) a filter comprising a proximal end and a distal end, a plurality of struts extending therebetween, and a porous covering permanently attached to said struts, with said proximal end of said filter attached to said distal end of said guidewire, and said distal end of said filter attached near said distal end of said core wire;
   f) said filter having a smaller first diameter for insertion into a vessel, and a second larger diameter for expanding to substantially equal the diameter of said lumen and to be placed in generally sealing relationship with said lumen;
   g) said filter attaining said smaller first diameter when said spacer is removed, said core wire is coaxially disposed within said guidewire and said distal end of said core wire is positioned at its maximum distance from said distal end of said guidewire;
   h) said filter attaining said larger second diameter when said core wire is slidably retracted through said guidewire, and said spacer is mounted onto said core wire in a longitudinal direction such that said proximal end of said spacer is substantially in contact with said distal end of said end cap, and said distal end of said spacer is substantially in contact with said proximal end of said guidewire.

2. The removable vascular filter system according to claim 1, wherein said guidewire is made from a superelastic Nickel-Titanium alloy.

3. The removable vascular filter system according to claim 1, wherein said end cap is made from a metallic material.

4. The removable vascular filter system according to claim 1, wherein said spacer is made from a polymeric material.

5. The removable vascular filter system according to claim 1, wherein said spacer is in operational correspondence with a predetermined filter diameter.

6. The removable vascular filter system according to claim 1, wherein said system comprises a plurality of spacers of different lengths, in operational correspondence with a plurality of predetermined filter diameters.

7. The removable vascular filter system according to claim 1, wherein said spacer is held in place by a snap or friction fit.

8. The removable vascular filter system according to claim 1, wherein said filter is made from superelastic Nickel-titanium alloy.

9. The removable vascular filter system according to claim 1, wherein said filter comprises a proximal end and a distal end, and a plurality of longitudinal struts extending therebetween.

10. The removable vascular filter system according to claim 1, wherein said filter comprises a proximal end and a distal end, and a plurality of circumferential struts extending therebetween.

11. The removable vascular filter system according to claim 1, wherein said filter comprises a proximal end and a distal end, and a plurality of hingedly connected struts extending therebetween.

12. The removable vascular filter system according to claim 1, wherein the pore size of said porous covering is from about 20 to about 300 microns.

13. The removable vascular filter system, according to claim 1, wherein said porous covering is a flexible polymeric material comprising regularly-spaced laser-formed holes therein.

14. The removable vascular filter system according to claim 13, wherein said flexible polymeric material is chosen from a group consisting of polyurethane, polyethylene or a co-polymer thereof.

15. The removable vascular filter system according to claim 13, wherein said flexible polymeric material is an elastomeric material capable of stretching to achieve said larger second diameter of said filter.

16. The removable vascular filter system according to claim 13, wherein said flexible polymeric material is folded when said filter achieves said smaller first diameter, and unfolds when said filter achieves said second larger diameter.

17. The removable vascular filter system according to claim 13, wherein the pore size of said porous covering is from about 20 to about 300 microns.

18. Method for capturing embolic particulates within the lumen of a vessel during a medical procedure, while allowing for continuous perfusion of blood, comprising the steps of:

a) providing a guidewire comprising a proximal end and a distal end; a generally solid core wire having a proximal end and a distal end, with said distal end of said core wire slidably inserted into said proximal end of said guidewire and advanced until said distal end of said core wire extends beyond said distal end of said guidewire; a filter comprising a proximal end and a distal end, a plurality of struts extending therebetween, and a porous covering permanently attached to said struts, with said proximal end of said filter attached to said distal end of said guidewire and said distal end of said filter attached near said distal end of said core wire; said filter having a smaller first diameter for insertion into a vessel and a second larger diameter for expanding to substantially equal the diameter of said lumen and to be placed in generally sealing relationship with said lumen; an end cap attached to said proximal end of said core wire, and a spacer, having a proximal end and a distal end, said spacer removably mountable onto said proximal end of said core wire;

b) inserting said guidewire into said lumen of said vessel until said distal end of said core wire is positioned past an occlusion in said vessel;

c) retracting said core wire until said spacer can be mounted onto said proximal end of said core wire, with said proximal end of said spacer substantially in contact with said distal end of said end cap and said distal end of said spacer substantially in contact with said proximal end of said guidewire, such that said filter substantially achieves said second larger diameter;

d) advancing additional devices over said guidewire, and positioning said devices at the site of said occlusion in said vessel;

e) performing additional procedures to therapeutically treat said occlusion in said vessel;

f) capturing embolic particulates generated by said procedures in said filter;

g) removing said interventional devices from said guidewire;

h) removing said spacer from said core wire;

i) advancing said core wire until said distal end of said core wire is at its maximum distance from said distal end of guidewire, said end cap is adjacent to but not in contact with said proximal end of said guidewire, and said filter substantially achieves said smaller first diameter; and j) removing said guidewire and said filter from said lumen, with said embolic particulates captured inside said filter.

19. For use with a removable vascular filter system attached to a guidewire, said system having a proximal end and a distal end, the improvement comprising:

a spacer having a proximal end and a distal end, said spacer removably mounted onto said system proximal end and said spacer movable in a longitudinal direction such that said proximal end of said spacer is substantially in contact with said proximal end of said filter system.

20. The removable vascular filter system according to claim 19, wherein said spacer is in operational correspondence with a predetermined filter diameter.

21. The removable vascular filter system according to claim 19, wherein said spacer is made from a polymeric material.

22. The removable vascular filter system according to claim 19, wherein said system comprises a plurality of spacers of different lengths, in operational correspondence with a plurality of predetermined filter diameters.

* * * * *